US011638794B2

(12) United States Patent
Genosar

(10) Patent No.: US 11,638,794 B2
(45) Date of Patent: May 2, 2023

(54) INTRANASAL PRESSURE DRUG DELIVERY DEVICE

(71) Applicant: AKTIVAX, INC., Broomfield, CO (US)

(72) Inventor: Amir Genosar, Broomfield, CO (US)

(73) Assignee: Aktivax, Inc., Broomfield, CO (US)

( * ) Notice: Subject to any disclaimer, the term of this patent is extended or adjusted under 35 U.S.C. 154(b) by 441 days.

(21) Appl. No.: 16/661,824

(22) Filed: Oct. 23, 2019

(65) Prior Publication Data

US 2020/0121871 A1 Apr. 23, 2020

Related U.S. Application Data

(60) Provisional application No. 62/749,296, filed on Oct. 23, 2018.

(51) Int. Cl.
*A61M 15/08* (2006.01)
*A61M 15/00* (2006.01)

(52) U.S. Cl.
CPC ........ *A61M 15/08* (2013.01); *A61M 15/0025* (2014.02); *A61M 15/0063* (2014.02); *A61M 15/0086* (2013.01)

(58) Field of Classification Search
CPC ........... A61M 15/00–0003; A61M 15/08–085; A61M 15/0021–004; A61M 15/0045; A61M 15/0063; A61M 15/0086; A61M 2209/08; A61M 11/00; A61M 11/006–02; A61M 11/06; A61M 11/008; A61M 2202/0225; A61M 2205/8225; A61M 2205/581; A61M 2205/582
See application file for complete search history.

(56) References Cited

U.S. PATENT DOCUMENTS

| 3,308,818 A | | 3/1967 | Rutkowski | |
| 3,733,010 A | * | 5/1973 | Riccio | ..................... B05B 11/06 |
| | | | | 222/635 |
| 3,788,526 A | * | 1/1974 | Thornton | ............... A61M 11/06 |
| | | | | 222/631 |

(Continued)

FOREIGN PATENT DOCUMENTS

| GB | 2255918 A | 11/1992 |
| JP | 2006230467 A | 9/2006 |

(Continued)

OTHER PUBLICATIONS

"Extended Europoean Search Report issued in European Patent Appliaction No. 19876316.1", dated Jul. 13, 2022, 9 pages.

(Continued)

*Primary Examiner* — Rachel T Sippel
*Assistant Examiner* — Jacqueline M Pinderski
(74) *Attorney, Agent, or Firm* — Holzer Patel Drennan

(57) ABSTRACT

A beneficial agent dispensing device comprises a dispenser body comprising a pressure chamber and at least one dispensing port. A flexible primary container stores the beneficial agent contained within the body. The arrangement is such that pressure in the pressure chamber depress the flexible primary container to expel the beneficial agent through the dispensing port. The beneficial agent dispenser can be configured to deliver the beneficial agent intranasally.

20 Claims, 3 Drawing Sheets

(56) References Cited

U.S. PATENT DOCUMENTS

| | | | | |
|---|---|---|---|---|
| 5,349,947 | A * | 9/1994 | Newhouse | B65D 83/06 |
| | | | | 128/203.15 |
| 5,875,776 | A * | 3/1999 | Vaghefi | A61M 15/0048 |
| | | | | 128/203.15 |
| 6,013,050 | A * | 1/2000 | Bellhouse | A61M 5/3015 |
| | | | | 604/68 |
| 6,045,534 | A * | 4/2000 | Jacobsen | A61N 1/30 |
| | | | | 604/140 |
| 6,125,844 | A * | 10/2000 | Samiotes | A61M 15/0065 |
| | | | | 128/200.12 |
| 6,186,141 | B1 * | 2/2001 | Pike | A61B 18/1206 |
| | | | | 128/203.12 |
| 2002/0056760 | A1 * | 5/2002 | Piper | A61M 15/0028 |
| | | | | 239/8 |
| 2003/0047571 | A1 | 3/2003 | Ramsey et al. | |
| 2003/0233070 | A1 | 12/2003 | De et al. | |
| 2005/0165349 | A1 * | 7/2005 | Stamp | A61M 5/30 |
| | | | | 604/70 |
| 2007/0052139 | A1 | 3/2007 | Gilbert | |
| 2008/0103490 | A1 * | 5/2008 | Edwards | A61M 5/2046 |
| | | | | 604/890.1 |
| 2010/0331765 | A1 * | 12/2010 | Sullivan | A61M 11/06 |
| | | | | 604/24 |
| 2016/0193412 | A1 * | 7/2016 | Cereda | A61M 5/2033 |
| | | | | 604/125 |
| 2017/0246393 | A1 * | 8/2017 | Genosar | A61M 5/008 |
| 2017/0305604 | A1 | 10/2017 | Sessions | |
| 2017/0368272 | A1 | 12/2017 | Glynn | |
| 2018/0085527 | A1 | 3/2018 | Taylor et al. | |

FOREIGN PATENT DOCUMENTS

| | | |
|---|---|---|
| KR | 20170130294 A | 11/2017 |
| WO | 1998017332 A2 | 4/1998 |
| WO | 2016033242 A1 | 3/2016 |
| WO | 2016058009 A2 | 4/2016 |
| WO | 2020086752 A1 | 4/2020 |

OTHER PUBLICATIONS

"First Exam report issued in related Indian Patent Application No. 202117019323", dated Sep. 12, 2022, 6 pages.

"First Office Action issued in Chinese Patent Application No. 201980080403.2", dated Jul. 14, 2022, 19-pages.

"International Search Report and Written Opinion", issued in PCT/US2019/057714, dated Feb. 7, 2020, 8 pages.

* cited by examiner

INTRANASAL PRESSURE DRUG DELIVERY DEVICE

CROSS-REFERENCE TO RELATED APPLICATION(S)

This application claims the benefit of U.S. Provisional Patent Application No. 63/749,296 filed Oct. 23, 2018 and is incorporated herein by reference in its entirety.

TECHNICAL FIELD

The present disclosure generally relates to dispensing packages. More specifically, the disclosure relates to intranasal drug delivery devices.

BACKGROUND

Intranasal dispensers, such as those used to administer Narcan®, utilize manual force to create a spray or jet of beneficial agent contained in the device. This results in potential variation in the dispensed flow characteristics depending on how strong and/or how fast the dispenser is operated. This irregularity in the flow characteristics may also result in varying drug absorbance and effectiveness.

Previously known intranasal dispensers use a syringe style form factor (i.e., barrel and piston arrangement). One drawback of such dispensers is that the exposure of the beneficial agent with materials associated with syringes such as silicone and rubber may compromise the beneficial agent's stability and effectiveness. Glass syringes can also compromise the device's tolerance to impact.

Accordingly, a need exists for improved intranasal dispensers that address some or all of the issued discussed above.

BRIEF DESCRIPTION OF THE DRAWINGS

FIG. 1a is an elevational view of an intranasal dispenser according to an exemplary embodiment, and showing the dispenser in a pre activation configuration;

FIG. 1b is a cross-sectional view of the intranasal dispenser as viewed about line 1b-1b in FIG. 1a;

FIG. 2a is an elevational view of the intranasal dispenser in an activated configuration;

FIG. 2b is a cross-sectional view of the intranasal dispenser as viewed about line 2b-2b in FIG. 2a;

DETAILED DESCRIPTION

Described herein are various embodiments of a beneficial agent dispenser comprising a body and at least one dispensing port. A pressure chamber is located in the body. Beneficial agent is stored in a flexible primary container located within the body. In some embodiments, the primary container may be a blister pack made from at least one of a film and a foil. Pressure in the pressure chamber depresses the primary container causing the beneficial agent to expel through the dispensing port. A pressure source causes the pressure chamber to pressurize. In some embodiments, the pressure source is a relatively small $CO_2$ cartridge having a rupturable membrane. A rupturable pin may be located in front of the rupturable membrane. The rupturing pin ruptures the rupturable membrane when the two are moved toward each other in a relative motion. A handle associated with an activation mechanism may be used to initiate the relative motion to rupture the $CO_2$ cartridge and pressurize the pressure chamber.

The primary container may be a flexible or semi-flexible package including, e.g., molded containers, blow molded containers, a sachet, a pouch, a tube, or any combination thereof.

The dispensing port may be configured for a variety of applications including, topical, oral, sub-lingual, ocular, oraticular, and for inhalation. The dispensing port may be of a variety of forms, including, e.g., a jet nozzle, a spray nozzle, or a topical applicator such as a brush or sponge.

Pressure sources other than $CO_2$ cartridges may be used, including pressure sources wherein pressure results from a chemical reaction.

Figures 1A, 1B:
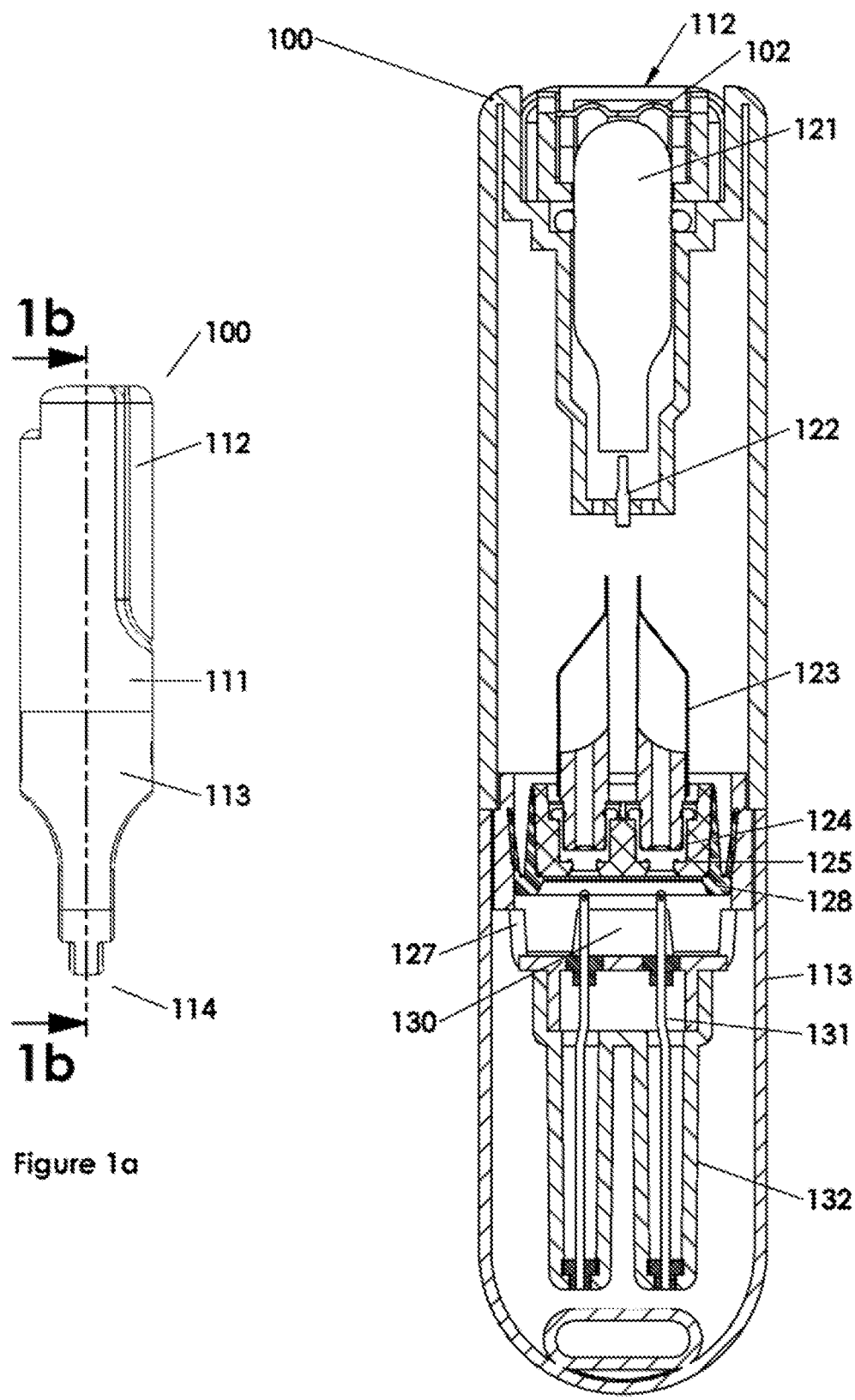

In some embodiments, the disclosed dispenser includes multiple primary containers containing the same or different beneficial agents. In other embodiments, the primary container comprises multiple compartments that can be manually or automatically merged prior to administration. In some embodiments, a first compartment comprises an active ingredient in dry format and a second compartment comprises a diluent, and the two compartments are merged prior to administration to allow the two substances to reconstitute and form the beneficial agent. The disclosed dispenser may comprise multiple primary containers, with the contents of each being dispensed through a common dispensing port. In some configurations, the disclosed dispenser includes multiple primary containers, the content of each is dispensed from a different dispensing port FIG. 1a illustrates an intranasal dispenser 100 according to various embodiments described herein. Intranasal dispenser 100 can include a body 111, a cap 113 attached to the body 111 at a proximal end 114, and an activation handle 112. The activation handle 112 communicates with an activation mechanism 102 (FIG. 1b).

FIG. 1b illustrates a cross section view of the intranasal dispenser 100 taken along line 1b-1b shown in FIG. 1a. The dispenser 100 includes a pressure chamber 110 within the body 111. The dispenser 100 further includes a $CO_2$ cartridge 121, wherein a distal end confronts a rupturing pin 122. The distal end of the cartridge 121 communicates with an activation mechanism 102, which can be manipulated by the handle 112. A piston 125 defines a proximal end of the pressure chamber 110 and is moveable between a pre-activation position (shown in FIG. 1b) and an activated position (shown in FIG. 2b). A first primary container 123 is located in the pressure chamber 110 and is connected to the piston 125. As noted previously, more than one primary container 123 can be located within the body 111, though FIG. 1b shows a single primary container 123. As shown in FIG. 1b, the primary container 123 is a blister pack made of a formed side, a lid, a flat side, and a fitment 124. The formed side and the lid side are peripherally sealed to each other, and each to the fitment 124 to form a sealed compartment. The fitment 124 is accommodated in an opening in the piston 125 in a seal tight fashion via seal 126. A piston seal 128 maintains a sealed connection between the piston 125 and the body 111. Venting windows 127 prevent pressure from building in the proximal end of the body 111. At the proximal end of the dispenser 100, a dispensing port 132 (shown in FIG. 1b in the form of a two-prone nasal applicator) extend from the body 111. A tube 131 runs inside the dispensing port 132 and communicates between the interior of the body 111 and the proximal end of the dispensing port 132. Cap 113 provides at least one of physical protection and aseptic enclosure to the dispensing port 132.

Figures 2A, 2B:
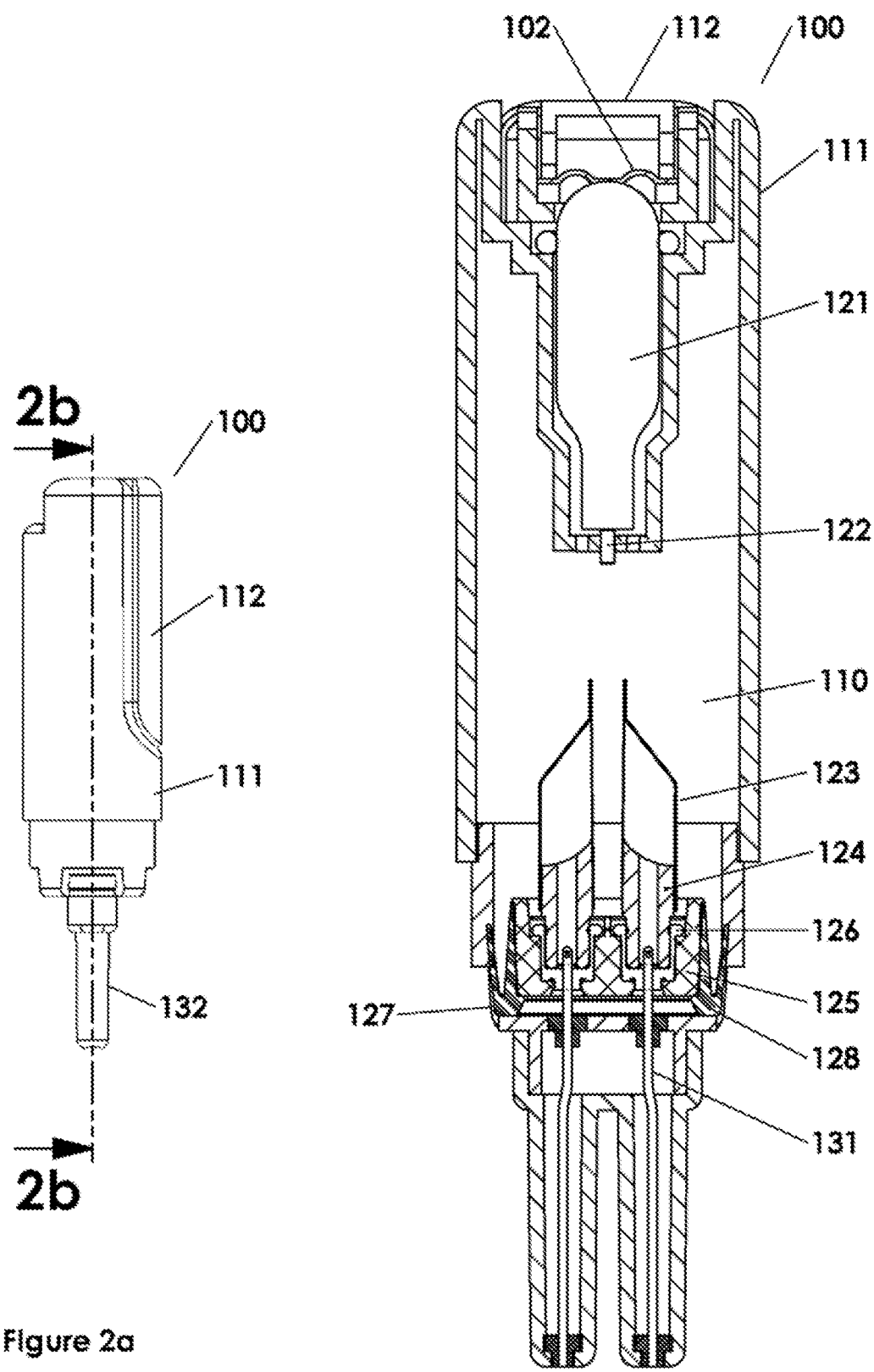

FIG. 2a illustrates the intranasal dispenser 100 in an activated position. To reach this configuration, the handle 112 is rotated away from the body 111 to draw back the activation mechanism 102, then depressed toward the body 111 to cause the activation mechanism 102 to rupture the $CO_2$ cartridge 121 against the rupturing pin 122 and thereby pressurize the pressure chamber 110. The cap 113 is removed to expose the dispensing port 132.

In FIG. 2b the activation mechanism 102 advances the $CO_2$ cartridge 121 such that the rupturing pin 122 is penetrated into the cartridge 121 allowing the $CO_2$ gas to pressurize the pressure chamber 110. The pressure advances the piston 125 toward the proximal end of the dispenser 100, to the activated position, causing the distal end of the tube 131 to penetrate the primary container 123, allowing the pressure to depress the primary container 123 and expel the content of the primary container 123 through the dispensing port 132. The seal 128 shows in the venting window 127, indicating that the device 100 has been actuated.

In some embodiments, a bleed hole opens when the seal 128 reaches the activated position, allowing the gas from the pressure chamber 110 to deplete and reduce the pressure. In some embodiments, a piston return spring (not shown) is disposed in vented chamber 130 (FIG. 1b), and the arrangement is such that after activation, when the pressure in the pressure chamber 110 is depleted under a certain threshold pressure, the spring force overcomes the force applied by the pressure in the pressure chamber 110, causing the piston 125 to retract and detach from the piston seal 128. The bleed hole serves as a timer for the piston dwelling time at the activated position such that faster bleed (e.g. larger bleed hole) will reduce the pressure in the pressure chamber 110 faster and the spring to retract the piston 125 earlier. The movement of the piston 125 from the pre-activation position to the activated position and back provides a tactile sensation to the user of the dispenser 100 from beginning to end. The bleeding of the pressure from the pressure chamber 110 provides the user with an audible sensation of the dispensing process from beginning to end. The ordinarily skilled artisan will recognize that a variety of dispensing devices can be accommodated at the proximal end of the dispensing port, such as a jet nozzle and a spray nozzle.

Figure 3A:
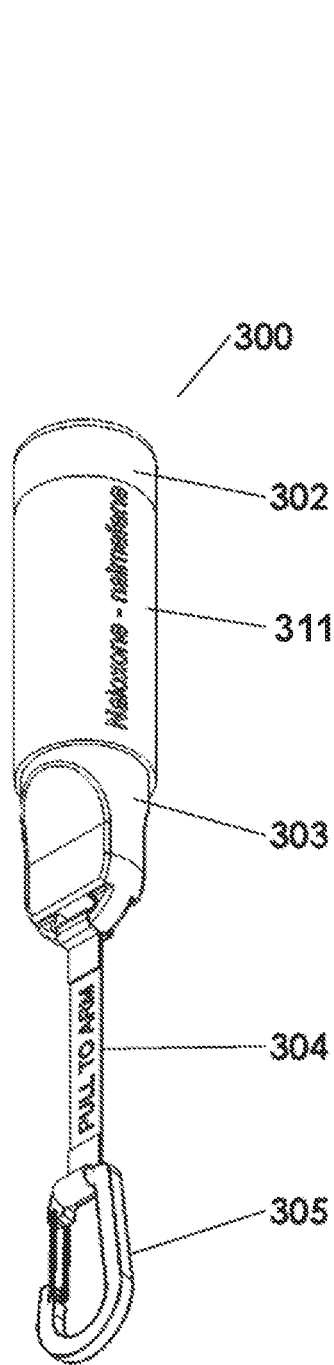
FIG. 3a is a perspective view of an intranasal dispenser with having a telescopic body.
Figure 3B:
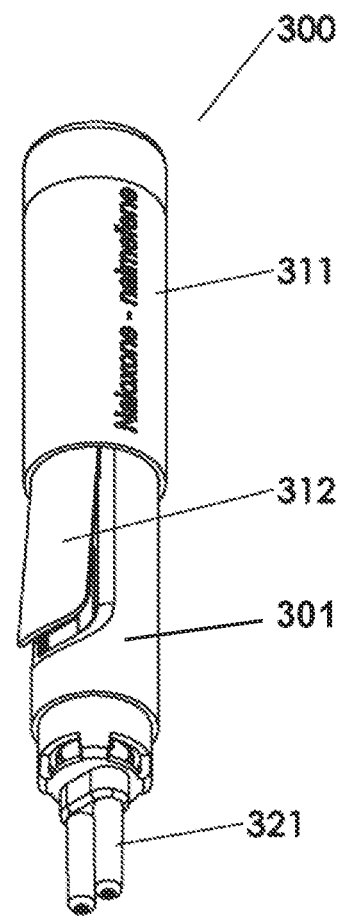
FIG. 3b is a perspective view of the intranasal dispenser of FIG. 3b and showing its cap removed.
Figure 3B:
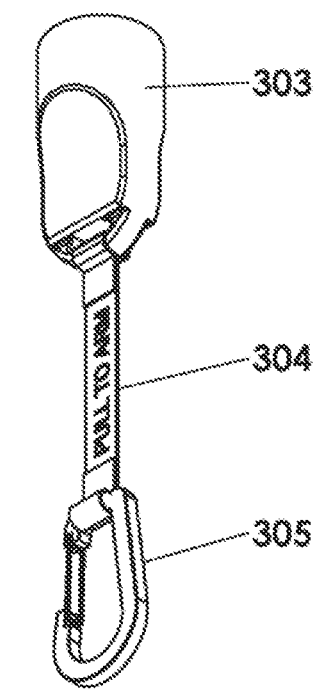

FIGS. 3a and 3b illustrate an intranasal dispenser 300 similar to the intranasal dispenser 100, comprising a telescopic body. The telescopic body includes a dispenser body 301 and a second body 311. A tether 304 is attached to the cap 303 on one end and a carabiner 305 on its other end. FIG. 3a illustrates the dispenser 300 when the telescopic body is collapsed, which may be more convenient for storage. By holding the second body 311 and pulling the tether 304 in the opposite direction of the second body 311, the telescopic body extends in an axial direction while the cap 305 is removed to expose the dispensing port 321, as shown in FIG. 3b. The arrangement is such that the proximal end of the second body 311 covers the distal end of the cap, preventing the cap from being removed until the telescopic body is extended. At the extended position, the handle 312 is allowed to move to the armed position for activation. The tether 304 is printed with information to facilitate user training and operation. The distal portion of the telescopic body is color coded to distinguish the dispenser 300 from other dispensers of different medications. In a similar fashion, at least one of the tether 304, the cap 303, and the carabiner 305 can be color coded. Moreover, the distal end 302 of the telescopic body can have a distinguished shape to help identify the treatment. The dispenser 300 facilitates operation of the dispenser 300 with limited dexterity or when wearing gloves as the extended telescopic body provides better gripping of the device, and the tether 304 with the carabiner 305 allows for easier holding and pulling than holding the cap 303 directly. For single-hand operation, the carabiner 305 can be attached to a firm object such as a garment, a carrying case, or a bag, and the extension of the telescopic body is done by merely pulling the second body 311. Details of the treatment can be printed on or attached to at least one of the tether 304, carabiner 305, or the cap 303. The carabiner 305 can be attached to the garment of a subject to indicate that the subject has been treated.

From the foregoing, it will be appreciated that specific embodiments of the invention have been described herein for purposes of illustration, but that various modifications may be made without deviating from the scope of the invention. Accordingly, the invention is not limited except as by the appended claims.

Although the technology has been described in language that is specific to certain structures and materials, it is to be understood that the invention defined in the appended claims is not necessarily limited to the specific structures and materials described. Rather, the specific aspects are described as forms of implementing the claimed invention. Because many embodiments of the invention can be practiced without departing from the spirit and scope of the invention, the invention resides in the claims hereinafter appended.

Unless otherwise indicated, all number or expressions, such as those expressing dimensions, physical characteristics, etc., used in the specification (other than the claims) are understood as modified in all instances by the term "approximately". At the very least, and not as an attempt to limit the application of the doctrine of equivalents to the claims, each numerical parameter recited in the specification or claims which is modified by the term "approximately" should at least be construed in light of the number of recited significant digits and by applying rounding techniques. Moreover, all ranges disclosed herein are to be understood to encompass and provide support for claims that recite any and all sub-ranges or any and all individual values subsumed therein. For example, a stated range of 1 to 10 should be considered to include and provide support for claims that recite any and all sub-ranges or individual values that are between and/or inclusive of the minimum value of 1 and the maximum value of 10; that is, all sub-ranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

I claim:

1. A beneficial agent dispensing device, comprising:
a primary container storing a beneficial agent; and
a dispenser body associated with the primary container and comprising a pressure chamber and a dispensing port, wherein applying a pressurized fluid in the pressure chamber causes penetration of the primary container and wherein the applied pressurized fluid is applied to the primary container to flex the primary container and expel the beneficial agent through the dispensing port,
wherein the dispensing port is fixedly attached to the dispenser body to prevent motion of the dispensing port relative to the dispenser body, and wherein the dispensing port comprises a fluid pathway providing fluid communication between an interior of the dispenser body and an external environment prior to pressurization.

2. The beneficial agent dispensing device of claim 1 wherein said primary container comprises a blister pack.

3. The beneficial agent dispensing device of claim 2 wherein said blister pack is formed from at least one of a film and a foil.

4. The beneficial agent dispensing device of claim 1 further comprising a pressurized fluid source adapted to provide the applied pressurized fluid.

5. The beneficial agent dispensing device of claim 4 wherein the pressurized fluid source includes a compressed gas cartridge comprising a rupturable membrane and a rupturing pin.

6. The beneficial agent dispensing device of claim 5 further comprising:
an activation mechanism comprising a horizontal plate and a handle disposed to actuate said activation mechanism and to actuate the compressed gas cartridge into the rupturing pin.

7. The beneficial agent dispensing device of claim 1 wherein said primary container comprises a flexible or semi-flexible package.

8. The beneficial agent dispensing device of claim 7 wherein said primary container comprises at least one or more of a blister pack, a molded container, a blow molded container, a sachet, a pouch, a tube, or any combination thereof.

9. The beneficial agent dispensing device of claim 1 wherein said dispensing port comprises at least one of a jet nozzle, a spray nozzle, or a topical applicator.

10. The beneficial agent dispensing device of claim 1, further comprising another primary container storing a common beneficial agent to the primary container or a different beneficial agent.

11. The beneficial agent dispensing device of claim 1 wherein said primary container comprises a plurality of compartments whose contents are merged upon activation of the dispensing device to reconstitute and form the beneficial agent.

12. The beneficial agent dispensing device of claim 1 further comprising:
a plurality of primary containers including the primary container, wherein contents of the plurality of primary containers are dispensed through said dispensing port.

13. The beneficial agent dispensing device of claim 1 further comprising a cap removably attached to said dispenser body.

14. The beneficial agent dispensing device of claim 1 further comprising a movable activation handle associated with said pressure chamber.

15. The beneficial agent dispensing device of claim 14 further comprising a piston associated with said pressure chamber and movable upon actuation of said handle from a pre-activation position to an activation position.

16. The beneficial agent dispensing device of claim 15 further comprising a piston return spring that is biased to retract the piston and urge the piston into the pre-activation position.

17. The beneficial agent dispensing device of claim 1 further comprising a bleed hole to assist in regulating pressure within said pressure chamber.

18. The beneficial agent dispensing device of claim 1 further comprising:
a tether comprising a connection between a removable cap and a connector, wherein said connector is configured to attach to a firm object.

19. The beneficial agent dispensing device of claim 18, further comprising:
a second body, wherein the dispenser body is able to retract into or extend from the second body, wherein a retracted configuration of the second body covers said cap so as to prevent said cap from being removed in the retracted configuration; and
wherein an extended configuration permits removal of said cap.

20. The beneficial agent dispensing device of claim 18, wherein said connector is a carabiner.

* * * * *